(12) United States Patent
Ito et al.

(10) Patent No.: US 7,067,471 B2
(45) Date of Patent: Jun. 27, 2006

(54) PROCESS FOR PRODUCING A REFINED PRODUCT OF POLYOXYPROYLENE FATTY ACID ISOPROPANOLAMIDE SURFACTANT

(75) Inventors: Toyofumi Ito, Kawagoe (JP); Hiroshi Higuchi, Kawagoe (JP)

(73) Assignee: Kawaken Fine Chemicals Co., Ltd., Tokyo (JP)

( * ) Notice: Subject to any disclaimer, the term of this patent is extended or adjusted under 35 U.S.C. 154(b) by 34 days.

(21) Appl. No.: 11/098,370

(22) Filed: Apr. 5, 2005

(65) Prior Publication Data
US 2005/0187135 A1 Aug. 25, 2005

Related U.S. Application Data

(62) Division of application No. 10/332,092, filed as application No. PCT/JP01/05821 on Jul. 4, 2001.

(30) Foreign Application Priority Data
Jul. 4, 2000 (JP) .............................. 2000-206859

(51) Int. Cl.
*C11D 3/20* (2006.01)
*C11D 3/32* (2006.01)

(52) U.S. Cl. ...................... 510/502; 510/126; 510/130; 564/192; 564/204; 564/215

(58) Field of Classification Search ...................... None
See application file for complete search history.

(56) References Cited

U.S. PATENT DOCUMENTS 6,514,918 B1  2/2003  Librizzi ....................... 510/124

FOREIGN PATENT DOCUMENTS

| EP | 0 450 527 | 10/1991 |
| JP | 56-82895 | 7/1981 |
| WO | WO 99/46356 | 9/1999 |

OTHER PUBLICATIONS

JP 05078294 (English Abstract Only), Publication Date: Mar. 30, 1993.
Database CA Online! Chemical Abstracts Service, Columbus, Ohio, US; Fujii, Tamotsu et al., "Polyoxypropylene-fatty acid isopropanol amide mixtures and manufacture thereof and chemical agents containing the same for detergents and cosmetics", XP002346281, retrieved from STN Database accession No. 126:187653.

*Primary Examiner*—Gregory R. Del Cotto
(74) *Attorney, Agent, or Firm*—Armstrong, Kratz, Quintos, Hanson & Brooks, LLP

(57) ABSTRACT

A refined product of a polyoxypropylene fatty acid isopropanolamide surfactant, having a high stability in storage and a very small change in smell thereof, is obtained by heat-treating an addition-reaction mixture prepared from a compound of the formula (III) and propylene oxide in a molar amount of 0.5 to 10 times that of the compound of the formula (III), and containing the target compound of the formula (I) and an oxazoline compound of the formula (II) produced as a by-product with water or an alkaline aqueous solution at 50 to 100° C., to hydrolyze the oxyazoline compound and to control the content of the oxyazoline compound to 0.1% by mass or less; and a detergent composition containing the refined product in a content of 1 to 50% by mass, exhibits enhanced thickening, foaming, emulsifying, dispersing and dissolving properties.

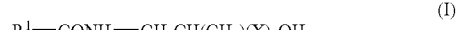

(I)

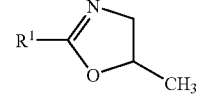

(II)

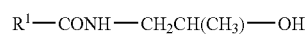

(III)

[$R^1$=$C_1$–$C_{19}$alkyl or alkenyl group, X=oxypropylene group, n=average number of addition-reacted X groups of 0.5 to 10]

3 Claims, No Drawings

PROCESS FOR PRODUCING A REFINED PRODUCT OF POLYOXYPROYLENE FATTY ACID ISOPROPANOLAMIDE SURFACTANT

This application is a divisional of U.S. patent application Ser. No. 10/332,092, filed Jan. 3, 2003, which is a 371 National Stage Application of PCT/JP01/05821, filed Jul. 4, 2001, and which is hereby incorporated by reference.

TECHNICAL FIELD

The present invention relates to a refined product of a polyoxypropylene fatty acid alkanolamide surfactant, a process for producing the same and a detergent composition containing the same.

BACKGROUND ART

Currently, surfactants for detergent are required to exhibit not only a high detergency but also high environmental adaptability and safety and low irritation property. From this point of view, practical utilization of fatty acid amide surfactants, having excellent biodegradability and safety, has been investigated. Among these investigations, a practical utilization of polyoxypropylene fatty acid isopropanolamide surfactant as a specific type of the fatty acid amide surfactants having very low irritation property has been studied.

Japanese Unexamined Patent Publication No. 9-20740 discloses polyoxypropylene fatty acid isopropanolamide surfactants. The polyoxypropylene fatty acid isopropanolamide surfactants have, in the molecular structure thereof, a secondary amide bond (—CONH—) which is chemically stable, and thus exhibit excellent stability over a wide range of pH value. Also, the polyoxypropylene fatty acid isopropanolamide surfactants exhibit excellent thickening performance, foam-enhancing performance, foam-stabilizing performance, emulsifying performance, dispersing performance and solubilizing performance. However, the surfactants are disadvantageous in color stability and the smell thereof. Thus, for the practical utilization of the surfactants, these disadvantages must be removed. Further, the polyoxypropylene fatty acid alkanolamide surfactants produced in accordance with the production process disclosed in the Japanese publication may exhibit a sensitivity under same conditions of the production process, and thus it is strongly desired that the cause of the sensitivity is investigated and the process is improved.

DISCLOSURE OF THE INVENTION

An object of the present invention is to provide a refined product of a polyoxypropylene fatty acid isopropanolamide surfactant having high safety, no change in color over a long time period and no or little smell, while retaining excellent thickening performance, foam-enchancing performance, foam-stabilizing performance, emulsifying performance, dispersing performance and solubilizing performance thereof, a process for producing the same and a detergent composition containing the same.

The inventors of the present invention synthesized the polyoxypropylene fatty acid isopropanolamide surfactants under various conditions and analyzed the resultant product, to attain the above-mentioned object. As a result, it was found that the stability of color and smell, and sensitivity of the synthesized polyoxypropylene fatty acid isopropanolamide surfactant are established in response to the content of oxazoline compounds produced as by-products and contained in the resultant polyoxypropylene fatty acid isopropanolamide.

Also, it was found that the content of the oxazoline compounds produced as by-products in the production of the polyoxypropylene fatty acid isopropanolamide is established in response to the reaction conditions under which propylene oxide is addition-reacted to a fatty acid isopropanolamide, and the oxazoline compounds can be easily hydrolyzed to such an extent that the stability of color and smell, and the sensitivity of the surfactant do not change by subjecting the polyoxypropylene fatty acid isopropanolamide surfactant containing oxazoline compounds to a heat reaction with water or an alkaline aqueous solution. The present invention was completed on the basis of this finding.

The refined product of polyoxypropylene fatty acid isopropanolamide surfactant of the present invention comprises, as a principal component, a surface active polyoxypropylene fatty acid isopropanolamide compound represented by the general formula (I):

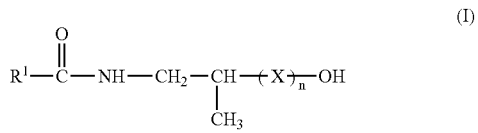

in which formula (I), $R^1$ represents an alkyl or alkenyl group having 5 to 19 carbon atoms, x represents an oxypropylene group and n represents an average number of the addition reacted X groups of 0.5 to 10.0 per molecule of the compound, and is characterized in that the content of oxazoline compounds represented by the general formula (II):

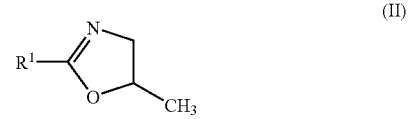

in which formula (II), $R^1$ is as defined above and contained, as impurities in the refined product is controlled to 0.1% by mass or less based on the mass of the compound of the above-mentioned formula (I).

In the refined product of the polyoxypropylene fatty acid isopropanolamide surfactant, the surface active polyoxypropylene fatty acid isopropanolamide compound represented by the general formula (I) and the oxazoline compound represented by the general formula (II) can be ones made by an addition-reaction of a fatty acid isopropanolamide represented by the general formula (III):

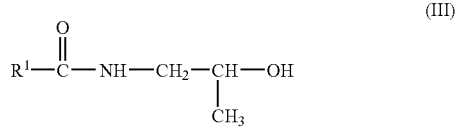

in which formula (III), $R^1$ is as defined above, with propylene oxide in an average amount of 0.5 to 10 moles per mole of the compound of the formula (III).

The process of the present invention for producing a refined product of a polyoxypropylene fatty acid isopropanolamide surfactant is characterized by addition reacting a fatty acid monoisopropanolamide represented by the general formula (III):

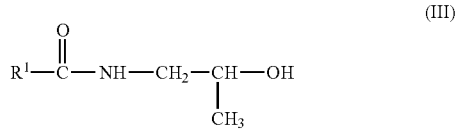

(III)

in which formula (III), R¹ represents an alkyl or alkenyl group having 5 to 19 carbon atoms with propylene oxide in a molar amount of 0.5 to 10 times that of the compound of the formula (III), to produce a reaction mixture of a surface active polyoxypropylene fatty acid isopropanolamide compound of the general formula (I) with, as a side reaction product, an oxazoline compound of the formula (II):

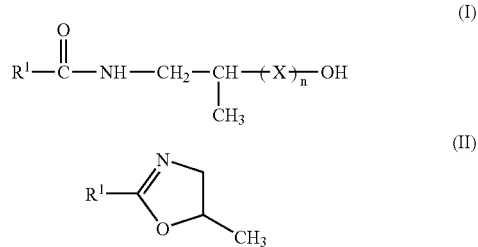

in which formulae (I) and (II), R¹ is as defined above, X represents an oxypropylene group and n represents an average number of moles of the addition-reacted X group of 0.5 to 10;

mixing water or an aqueous alkaline solution into the reaction mixture, to prepare a refining reaction system;

heating the refining reaction system to a temperature of 50 to 100° C. to hydrolyze the oxazoline compound of the general formula (II) and to thereby reduce the content of the oxazoline compound of the general formula (II) in the reaction mixture to 0.1% by mass or less based on the mass of the compound of the formula (I); and collecting the refined product of surface active polyoxypropylene fatty acid isopropanolamide surfactant comprising the compound of the formula (I) from the reaction system.

In the process of the present invention for producing a refined product of the surface active polyoxypropylene fatty acid isopropanolamide surfactant, the pH value of the refining reaction system is preferably adjusted to 7.5 to 12.0.

In the process of the present invention for producing a refined product of the surface active polyoxypropylene fatty acid isopropanolamide surfactant, the aqueous alkaline solution to be contained in the refining reaction system is preferably selected from aqueous solutions of at least one member selected from sodium hydroxide, potassium hydroxide and lithium hydroxide.

The detergent composition of the present invention comprises the refined product of the polyoxypropylene fatty acid isopropanolamide surfactant in a content of 0.1 to 50% by mass.

BEST MODE OF CARRYING OUT THE INVENTION

The refined product of the surfactant of the present invention is a refined product of the polyoxypropylene fatty acid isopropanolamide surfactant represented by the general formula (I).

In the compound of the general formula (I), the average number n of the addition-reacted oxypropylene groups X is 0.5 to 10, preferably 0.7 to 5.0, more preferably 0.7 to 2.0 per molecule of the compound. If the average number n is less than 0.5, the obtained refined product of the surfactant compound exhibits a decreased stability at a low temperature and an increased melting temperature and thus a composition containing the resultant refined product of the surfactant compound exhibits an unsatisfactory handing property. Also, if the average number n is more than 10, the characteristic advantage of the surfactant-refined product of the present invention that a viscosity-increasing effect on the surfactant composition is high becomes insufficient.

The polyoxypropylene fatty acid isopropanolamide surfactant compound of the formula (I) includes:

polyoxypropylene (1) lauric acid isopropanolamide,
    polyoxypropylene (1.5) lauric acid isopropanolamide,
    polyoxypropylene (2) lauric acid isopropanolamide,
    polyoxypropylene (5) lauric acid isopropanolamide,
    polyoxypropylene (1.5) myristic acid isopropanolamide,
    polyoxypropylene (3) myristic acid isopropanolamide,
    polyoxypropylene (2) oleic acid isopropanolamide,
    polyoxypropylene () oleic acid isopropanolamide,
    polyoxypropylene (0.8) coconut oil fatty acid isopropanolamide,
    polyoxypropylene (1) coconut oil fatty acid isopropanolamide,
    polyoxypropylene (1.4) coconut oil fatty acid isopropanolamide,
    polyoxypropylene (1.8) coconut oil fatty acid isopropanolamide,
    polyoxypropylene (1) palm oil fatty acid isopropanolamide,
    polyoxypropylene (2) palm oil fatty acid isopropanolamide,
    polyoxypropylene (5) palm oil fatty acid isopropanolamide.

The above-mentioned polyoxypropylene fatty acid isopropanolamide surfactant compounds are usually produced by addition-reacting propylene oxide to fatty acid monoisopropanolamide compounds represented by the formula (III).

The fatty acid monoisopropanolamide represented by the formula (III) can be produced by the conventional synthesis method using, as a starting material, fatty acids, fatty acid esters or fatty acid halides.

The fatty acid monoisopropanolamide can be easily produced by using, as a starting material, a fatty acid ester, by a process in which a lower alkyl ester of a fatty acid, represented by the general formula (IV):

(IV)

in which formula (IV), R¹ as defined above, and R² represent an alkyl group having 1 to 3 carbon atoms, is mixed with monoisopropanolamine in a mixing molar ratio of 1:1 to 1:1.2; the mixture is subjected to a reaction in absence of a catalyst or in the presence of a basic catalyst, for example, sodium methoxide, at a temperature of, for example, 80 to 200° C., preferably 80 to 120° C. under a reaction pressure of 1.3 kPa to 101.3 kPa, to prepare a monoisopropanolamide of the fatty acid represented by the formula (III); and non-reacted monoisopropanolamine remaining the reaction system is removed.

The lower alkylesters of fatty acids represented by the formula (IV) usable as a starting material for the above-mentioned reaction.

The lower alkylesters of fatty acids of the formula (IV) usable as starting materials for the process are selected from methyl laurate, ethyl laurate, isopropyl laurate, methyl myristate, ethyl myristate, methyl ester of coconut oil fatty acid, ethyl ester of coconut oil fatty acid, methyl ester of palm oil fatty acid and ethyl ester of palm oil fatty acid. These esters may be employed alone or in a mixture of two or more thereof. In consideration of easy availability, cost for obtaining and reactivity, the methyl esters of the above-mentioned fatty acids are preferably employed.

The fatty acid monoisopropanolamide can be easily produced from a fatty acid, by a process in which a mono-basic fatty acid having 6 to 20 carbon atoms is mixed with monoisopropanolamine in a molar ratio of 1:1 to 1:2 preferably 1:1 to 1:1.3; the mixture is subjected to a reaction in the presence or absence of a catalyst under conditions, for example, a temperature of 80 to 180° C., preferably 140 to 160° C., to prepare a fatty acid isopropanolamide represented by the formula (III); and the non-reacted monoisopropanolamide remaining in the reaction system is removed. The entire amount of the mixture may be subjected to the reaction or a plurality of portions of the mixture may be successively subjected to the reaction.

The fatty acids usable as starting materials for the above-mentioned process include lauric acid, mysristic acid, coconut oil fatty acid and palm oil fatty acid. These fatty acids may be employed alone or in a mixture of two or more thereof.

By addition-reacting propylene oxide to the fatty acid monoisopropanolamide of the formula (III) obtained by the above-mentioned process, a pqlyoxypropylene fatty acid monoisopropanolamide surfactant compound is obtained.

In the preparation of the polyoxypropylene fatty acid isopropanolamide surfactant compound of the general formula (I), propylene oxide is subjected in a molar amount of 0.5 to 10 times that of the fatty acid monoisopropanolamide subjected to the reaction. The amount of the propylene oxide addition-reacted with the fatty acid monoisopropanolamide reflects to the average number of the addition-reacted oxypropylene groups of the resultant polyoxypropylene fatty acid isopropanolamide. Therefore, the target average number of the addition reacted oxypropylene groups may be established in response to the purpose of the use of polyoxypropylene fatty acid isopropanolamide surfactant compound.

There is no specific limitation to the method of addition reaction of propylene oxide to a fatty acid monoisopropanolamide. As a catalyst for the addition reaction of propylene oxide, for example, Lewis acid catalysts such as boron trifluoride, titanium chloride and tin chloride; basic catalysts such as sodium hydroxide, potassium hydroxide, sodium methoxide and sodium ethoxide; and metal oxide composite such as calcined hydrotalcite and amorphous hydrotalcite, may be employed. In the process of the present invention, however, as an aqueous alkaline solution is preferably employed for the refining procedure, the above-mentioned basic catalysts are preferably employed as a catalyst for the above-mentioned addition reaction. Also, water or hydroxide ions may react with propylene oxide to produce, as a by product, propylene glycol, and thus a sodium alcoxide, for example, sodium methoxide or sodium ethoxide is preferably employed as a basic catalyst.

The addition reaction of propylene oxide can be effected at a temperature equal to or higher than the melting temperature of the fatty acid monoisopropanolamide, preferably of 80° C. to 180° C., more preferably 100 to 140° C. If the reaction temperature is less than 80° C., the reaction rate may be insufficient, and if the reaction temperature is more than 180° C., the resultant surface active compound mixture may be colored, and the color may not be removed even by applying a hydrolysis treatment with the oxazoline compound of the formula (II) to the surface active compound mixture in the next step. To prevent the coloration of the surface active compound mixture in the addition reaction step, it is effective that the air in the reactor is replaced by an inert gas before the reaction.

The charge of propylene oxide may be effected by any one of the following methods.

(a) The charge of propylene oxide is effected before heating.

(b) The propylene oxide is heated to a reaction temperature, and then charged in liquid state.

(c) The propylene oxide is heated to a reaction temperature, and then charged in gas state.

Since the addition reaction of propylene oxide is an exothermic reaction, the method (a) is disadvantageous in that the reaction temperature is difficult to control, and thus the methods (b) or (c) are preferred.

The surface active compound of the general formula (I) produced by the above-mentioned preparation process or a composition containing the same, is contaminated with the oxazoline compound of the general formula (II) which is produced as a by-product of the addition reaction and mixed thereinto, and effects on the stability on color of the reaction product.

The oxazoline compound of the general formula include 4-methyl-2-undecyl-2-oxazoline, 4-methyl-2-tridecyl-2-oxazoline, 4-methyl-2-heptyl-2-oxazoline and 4-methyl-2-nonyl-2-oxazoline.

These oxazoline compounds have a chemical structure (as shown in the general formula (II)) which is formed by an intramolecular dehydrate-condensation of the fatty acid monoisopropanolamide represented by the general formula (III).

In the investigation made by the inventors of the present invention, it was found that the oxazoline compound of the formula (II) is generated mainly under the synthetic conditions under which propylene oxide is addition-reacted with the fatty acid monoisopropanolamide rather than under a condition under which the fatty acid or fatty acid halide is converted to the fatty acid monoisopropanolamide. Particularly, when the addition reaction temperature is set up at 150° C. or more, the oxazoline compound is generated in an increased amount.

In a conventional synthetic method of addition reacting propylene oxide with a starting material consisting of a fatty acid monoisopropanolamide of the formula (III), the oxazoline compound of the formula (II) is produced as a by-product in an amount of 1 to 5% by mass under reaction conditions in practice in which the reaction temperature is 130° C. or more. The generation of the oxazoline compound of the formula (II) varies in response to the reaction conditions. It was found by the inventors of the present invention that if the by-product, oxazoline compound is present in an amount of more than 0.1% by mass in the surface active compound of the formula (I), the stability on color of the compound of the formula (I) and the composition of the compound is affected by the oxazoline compound.

The content of the oxazoline compound of the formula (II) contained in the refined product of the surface active compound is controlled to 0.1% by mass or less, preferably 0.05% by mass or less.

There is no specific limitation to the method of controlling the content of the oxazoline compound to the above-mentioned range.

The content of the oxazoline compound in the reaction product produced from the addition reaction of propylene oxide with the fatty acid monoisopropanolamide may be controlled to 0.1% by mass or less by controlling the reaction temperature to a low level of 100° C. or less. However, this low temperature reaction is disadvantageous in that the necessary reaction time is too long. To reduce the production amount of the oxazoline compound, a method in which the oxazoline compound is absorbed and removed by an absorber, for example, activated carbon, activated alumina and silica gel, is known. Otherwise, a method in which the oxazoline compound is modified by reduction and a method in which one of the above-mentioned methods is combined with a refining procedure, for example, a molecular distillation, is considered. However, in consideration of cost, reaction time and other factors, the refining process of the present invention in which the resultant oxazoline compound is hydrolyzed with water, more preferably an aqueous alkaline solution, is most advantageous.

The inventors of the present invention found that the oxazoline compound contained in a high content in the reaction system of the present invention for the polyoxypropylene fatty acid isopropanolamide can be easily decomposed by mixing water or an aqueous alkaline solution into the reaction mixture and heating, and the content of the oxazoline compound can be reduced to a level at which no problem of the stability in color of the reaction product occurs.

To produce the refined product of the polyoxypropylene fatty acid isopropanolamide surfactant, after the addition reaction of propylene oxide with a fatty acid monoisopropanolamide of the formula (III) is completed, the resultant reaction system is subjected to a refining treatment. Namely, the reaction system containing the polyoxypropylene fatty acid isopropanolamide surfactant is mixed with water or an aqueous alkaline solution, and then the resultant refining system is heated at a temperature of 50° C. to 100° C., to hydrolyze the oxazoline compound of the formula (II) contained, as a by-product, in the reaction system mixture and to thereby decrease the content of the oxazoline compound to a level of 0.1% by mass or less, based on the weight of the polyoxypropylene fatty acid isopropanolamide surfactant. Then, the refined product of the polyoxypropylene fatty acid isopropanolamide surfactant is collected from the refining system.

In the refining procedure, the alkaline substance to be added to the refining system is preferably selected from sodium hydroxide, potassium hydroxide, lithium hydroxide, magnesium hydroxide, calcium hydroxide, barium hydroxide and aluminum hydroxide.

To promote the hydrolysis reaction of the oxazoline compound, sodium hydroxide, potassium hydroxide or lithium hydroxide which is easily dissolved in water and can be easily controlled to a desired concentration, is preferably employed. More preferably, sodium hydroxide, potassium hydroxide or a mixture thereof which is readily available and cheap, is used for the hydrolysis of the oxazoline compound.

In the refining procedure of the process of the present invention, in the case where the amount of the alkaline substance added to the reaction system is too large, sometimes, the polyoxypropylene fatty acid isopropanol amide surface active compound of the formula (I) is hydrolyzed. Therefore, the alkaline substance is preferably added in an amount of from 0.001% by mass to 5% by weight, more preferably 0.01% by mass to 1% by mass, based on the weight of the reaction system containing the surface active compound.

There is no specific limitation to the amount of water used for the preparation of the aqueous alkaline solution. The amount of water must be sufficient to completely dissolve the alkaline substance therein to provide the aqueous alkaline solution. Usually, the amount of water is preferably 1% by mass to 10% by mass based on the weight of the reaction system containing the surface active compound.

The time period necessary to the hydrolysis of the oxazoline compound is variable in response to the hydrolysis temperature. Usually, the hydrolysis reaction is completed in a time of 15 minutes to 10 hours. The completion of the hydrolysis of the oxazoline compound can be easily detected by measuring the content of the oxazoline compound in the refining reaction product by a gas chromatographic or high performance liquid chromatographic analysis of the refining reaction product.

After the completion of the hydrolysis reaction of the oxazoline compound is confirmed, the refining reaction product may be directly employed as a material for a target detergent when the target detergent is allowed to contain water therein. If necessary, the refining reaction system is subjected to a reduced pressure treatment to distill away water contained in the refining reaction system. In this treatment, a small amount of residual propylene oxide in the reaction system can be removed, together with water, from the reaction system.

As a surface active compound similar in chemical structure to the polyoxypropylene fatty acid isopropanolamide nonionic surfactant, polyoxypropylene fatty acid monoethanolamide nonionic surfactants are known.

In the composition of the polyoxypropylene fatty acid monoethanolamide surfactant with the polyoxypropylene fatty acid isopropanolamide nonionic surfactant, provided that they are the same in the length of the oxypropylene chain and the type of the fatty acid as each other, substantially no difference in thickening property and foaming property appears between them.

However, the monoethanolamide structure contained in the polyoxypropylene fatty acid monoethanolamide nonionic surfactant causes the nonionic surfactant to exhibit a higher melting temperature than that of the polyoxypropylene fatty acid isopropanolamide nonionic surfactant. In this connection it was found that due to the high melting temperature, the polyoxypropylene fatty acid monoethanolamide surfactant exhibits a poorer handling property and a lower stability at low temperature when mixed into a detergent composition, than the polyoxypropylene fatty acid isopropanol amide non-ionic surfactant.

When the refined product of the surface active compound of the present invention is employed as a component of a detergent or cosmetic, the refined product may be mixed with one or more members selected from usual components for conventional detergents and cosmetics, for example, extracts derived from animal, vegetable, fish and shellfish and microorganism matters, powdery materials, liquid oil and fat materials, solid oils and fats, waxes, hydrocarbon oils, higher fatty acids, higher alcohols, esters, silicones, anionic surfactants, cationic surfactants, amphoteric surfactants, non-ionic surfactants, moisture-retaining agents, water-soluble polymers, thickening agents, coat-forming agents, ultraviolet ray absorbers, extinguishing agents, sequestrants, lower alcohols, saccharides, amino acid compounds, organic amine compounds, synthetic resin emulsions, pH-adjustors, skin-nutritive agents, vitamines, antioxidants, antioxidant-assistants, perfumes and water.

The extracts derived from animal, vegetable, fish, shellfish and microorganism matters include tea extracts, also extracts, ginkyo leaf extracts, Swertia japonica extracts, mugwort extracts, garlic extracts, Ougon extracts, rose-mary extracts, snake gourd extracts, placenta extracts, lactic acid bacillus-culture extracts and seaweed extracts.

The powdery materials include inorganic powders, for example, powders of talc, kaolin, mica, sericite, muscocite, phlogopite, synthetic mica, lepidolite, biotite, lithia mica, vermiclite, magnesium carbonate, zirconium silicate, aluminum silicate, barium silicate, calcium silicate, zinc silicate, magnesium silicate, strontium silicate metal salts of tungstic acid, magnesium, silica, zeolites, barium sulfate, calcined calcium sulfate (calcined gypsum), calcium phosphate, fluoroapatite, hydroxyapatite, ceramic powders, activated carbon, medical carbon, metal soaps (sodium myristate, calcium palmitate, aluminum stearate, etc.), and boron nitride; and organic powders, for example, powders of polyamide resins nylon powders), polyethylene resins, methyl methacrylate resins, polystyrene resins, styrene-acrylic acid copolymer resins, benzoquanamine resins, polyethylene tetrafluoride resins and cellulose.

The liquid oil and fat materials include avocado oil, Camellia Japonica oil, grape seed oil, turtle oil, macademia nut oil, corn oil, mink oil, olive oil, sunflower oil, vape seed oil, deutoplasm oil, sesame oil, persic oil, wheat embryo bud oil, sazanka oil, castor oil, linseed oil, saffron oil, cotton seed oil, perilla oil, soybean oil, peanut oil, tea sea oil, torreya nut oil, rice bran oil, chinese paulownia oil, Japanese paulownia oil, jojoba oil, embryo bud oil, triglycerol, glycerol trioctanate and glycerol triisopalmitate.

The solid oil and fat materials include cacao butter, coconut oil, horse fat, hardened coconut oil, palm oil, beef tallow, mutton tallow, hardened tallow, palm kernel oil, lard, ox bone oil, haze kernel wax hardened oil, ox leg wax, haze wax and hardened castor oil.

The waxes include beewax, candelilla wax, cotton, wax, carnauba wax, bay berry wax, insect wax, whale wax, montan wax, rice kran wax, lanolin, kapok wax, lanolin acetate, liquid lanolin, sugar cane wax, isopropyl ester of lanolin fatty acid, hexyl laurate, reduced lanolin, hard lanolin, shellac wax, POE lanolin alcohol ester, POE lanolin alcohol acetate, POE cholesterol ethers, polyethyleneglycol ester of lanolin fatty acid, POE and hydrogenated lanolin alcohol ether.

The hydrocarbon oils include liquid parafin, ozokerite, squalene, pristane, parafin, ceresin, squalane, petrolatan and microcrystalline waxes.

The higher fatty acids include lauric acid, myristic acid, palmitic acid, searic acid, behenic acid, oleic acid 12-hydroxystearic acid, undecylenic acid, tall oil fatty acid, coconut fatty acid, palm oil fatty acid, palm core fatty acid, isostearic acid, linoleic acid, linolenic acid, eicosapentaenoic acid and docosahexaenic acid.

The synthetic ester oils include isopropyl myristate, cetyl actanate, octyldodecyl myristate, isopropyl palmitate, butyl stearate, hexyl laulate, myristyl myristate, decyl oleate, hexyldecyl dimethyloctanate, cetyl lactate, myristyl lactate, lanolin acetate, isocetyl stearate, isocetyl isostearate, choresteryl 12-hydroxystearate, ethyleneglycol di-2-ethylhexylate, dipentaerythritol fatty acid ester, neopentylglycol caprate, diisostearyl malate, glycerol di-2-heptylundecate, trimethylolpropane tri-2-ethylhexylate, trimethylpropane triisostearate, pentaerythritol tetra-2-ethylhexylate, glycerol tri-2-ethylhexylate, trimethylolpropane triisostearate, cetyl-2-ethylhexanoate, 2-ethylhexylpalmitate, glycerol trimyristate, glyceride tri-2-heptylundecate, methyl ester of castor oil fatty acid, oleyl oleate, acetostearyl alcohol, acetoglyceride, 2-heptylundecyl palmitate, diisobutyl adipate, 2-octyldodecyl ester of N-lauroyl-L-glutamic acid, 2-heptylundecyl adipate, ethyl laurate, di-2-ethylhexyl sebacate, 2-hexyldecyl myristate, 2-hexyldecyl palmitate, 2-hexyldecyl adipate, diisopropyl sebacate, 2-ethylhexyl succinate, ethyl acetate, butyl acetate, amyl acetate and triethyl citrate.

The silicones include dimethyl silicone oil, methyl polysiloxane, octamethyl trisiloxane, methyl polysiloxane having a high degree of polymerization, decamethylpolysiloxane, dodecamethyl polysiloxane, tetramethyltetrahydrogene polysiloxane, dimethyl siloxane-methyl(polyoxyethylene) siloxane copolymers, dimethyl siloxane-methyl(polyoxyethylene)siloxane-methyl (polyoxypropylene)siloxane copolymers and amino-modified silicones.

The above-mentioned anionic surfactants include fatty acid soaps, for example, soap materials, sodium laurate, sodium palmitate, potassium coconut fatty acid soap; higher alkyl sulfate esters, for example, sodium laurylsulfate, potassium laurylsulfate, and triethanolamine laurylsulfate; salts of alkylether sulfate ester, for example, triethanolamine POE laurylsulfate and sodium POE laurlsulfate; salts of N-acylamino acids, for example, lauroylsulcosine sodium, lauroyl-β-alanine sodium, lauroyl-N-methyl-β-alanine sodium, monosodium N-lauroylglutamate, disodium N-stearoylglutamate, monosodium N-myristoyl-L-glutamate, diethanolamine N-palmitoylasparagate, N-lauroyl silk peptide, and coconut fatty acid silk peptide; salts of higher fatty acid amide sulfonic acids, for example, N-myristoyl-N-methyltaurin sodium, lauroylmethyl-taurin sodium; phosphate esters, for example, sodium POE oleylether phosphate, POE stearylether phosphoric acid and sodium POE laurylamideether-sphosphate; sulfosuccinate salts, for example, sodium di-2-ethylhexylsulfosuccinate, sodium monolauroylmonoethanolamide polyoxyethylenesulfosuccinate and sodium laurylpolypropyleneglycolsulfosuccinate; alkylbenzenesulfonate salts, for example, sodium linear dodecylbenzenesulfonate, triethanolamine linear dodecylbenzenesulfonate; salts of higher fatty acid ester sulfate esters, for example, sodium hardened coconut fatty acid glycerol sulfate; sulfated oils such as Turkey red oil, for example, α-olefin sulfonate salts, higher fatty acid ester sulfonate salts, and secondary alcohol sulfate ester salts; higher fatty acid alkyrolamidosulfate ester salts; sodium lauroyl monoethanolamidosuccinate; acrylisethionate salts; and casein sodium.

The above-mentioned cationic surfactants include alkyltrimethyl ammonium salts, for example, stearlytrimethyl ammonium chloride, lauryltrimethyl ammonium chloride, lauryltrimethyl ammonium bromide; dialkyldimethyl ammonium salts, for example, distearyldimethyl ammonium chroride; alkyl pyridinium salts, for example cetyl pyridinium chloride; and alkyldimethylbenzylammonium salts, benzethonium chloride and benzalkonium chloride.

The above-mentioned amphoteric surfactants include amideamine type amphoteric surfactants, for example, 2-undecyl-N-carboxymethyl-N-hydroxyethylimidazolium betaine, N-lauroyl-N'-carboxymethyl-N'-hydroxyethylethylenediamine sodium and N-coconut fatty acid aryl-N'-carboxyethyl-N'-hydroxyethylethylenediamine sodium; amide acetic acid betaine type amphoteric surfactants, for example, lauric acid amide propylbetaine, coconut fatty acid amide propylbetaine and myristic acid amide propylbetaine; amide sulfobetain type amphoteric surfactants, for example, lauric acid amide propyl hydroxysulfobetain; amine oxide type amphoteric surfactants, for example, lauryldimethylamine oxide and lauric acid amide propylamine oxide; and alkyl acetic acid betain type amphoteric surfactants and alkyl sulfobetain type amphoteric surfactants.

The above-mentioned non-ionic surfactants include glycerol esters of fatty acids, for example; glyceryl monostearate, sulf-emulsifying glyceryl monostearte and glyceryl monoisostearate; polyoxyethylene glycerol esters of fatty acids, for example, POE glycerol monostearate; POE glyceryl monooleate; polyglycerol ester of fatty acids, for example, diglycerol monostearate, tetraglyceryl tristearate, decaglyceryl pentastearate; sorbitol esters of fatty acids, for example, sorbitan monolaurate, sorbitan resquistearate and sorbitan monooleate; polyoxyethylenesorbitan esters of fatty acids, for example, POE sorbitan ester of mono-coconut fatty acid, POE sorbitan tristearate, and POE sorbitan trioleate; polyoxyethylene sorbitol esters of fatty acids, for example, POE sorbitol monolaurate, and POE sorbitoltetraoleate; polyethylene glycol esters of fatty acids, for example, polyethyleneglycol monolaurate, polyethyleneglycol monosterate, polyethyleneglycol monooleate, and polyethyleneglycol disterate; polyoxyethylene alkyl esters, for example, POE lauryl ether, POE cetyl ether, and POE stearyl ether; and polyoxyethylenepolyoxypropylene alkyl ethers, for example, POE•POP cetyl ether, POE•POP decyltetradecylether; polyoxyethylene alkylphenyl ethers, for example, POE nonylphenyl ether, POE octylphenyl ether, POE branched octylphenyl ether; polyoxyethylenealkylamines, for example, POE stearylamine, POE oleylamine; fatty acid alkanolamides, for example, coconut fatty acid diethanolamide, coconut fatty acid monoethanolamide, lauric acid diethanolamide, and palm core oil fatty acid diethanolamide; polyoxyethylene alkanolamides, for example, POE lauric acid monoethanol amide, POE coconut fatty acid monoethanolamide, and POE tallow fatty acid monoethanolamide; and acetylene glycol, POE acetylene glycol, POE lanolin, POE lanolin alcohol, POE castor oil, POE hardened castor oil, POE phytosterol, POE chorestanol, and POE nonylphenol-formaldehyde condensation product.

The above-mentioned moisture-retaining agents include glycerol, propyleneglycol, 1,3-butylene glycol, sorbitol, sodium lactate, pyrrolidone carboxylic acid and salts thereof.

The above-mentioned water-soluble polymers include quar gum, quince seed, pectin, gelatin, xanthane gum, methyl cellulose, ethyl cellulose, hydroxyethyl cellulose, hydroxypropyl cellulose, carboxymethyl cellulose and salts thereof, alginic acid salts, polyvinyl alcohol, carboxyvinyl polymers, sodium polyacrylate, bentonite, chitric, chitosan derivatives, hyaluronic acid and salts thereof, collagen and derivative thereof.

The above-mentioned thickening agents include coconut oil fatty acid monoethanolamide, lauric acid diethanolamide, lauric acid isopropanolamide, and polyoxyethylene coconut oil fatty acid monoethanolamide.

The above-mentioned coat-forming agents include polyvinyl alcohol, polyvinylpyrolidone, cation-modified cellulose, and silicones.

The above-mentioned ultraviolet ray-absorbers include benzophenone derivatives, for example, 2-hydroxy-4-methoxy-benzophenone, 2-hydroxy-4-methoxy-benzophenone-5-sulfonic acid and salt thereof and dihydroxydimethoxybenzophenone; p-aminobenzoic acid compounds, for example, p-aminobenzoic acid and ethyl p-aminobenzoate; methoxy cinamic acid derivatives, for example, ethyl p-methoxycinamate, isopropyl p-methoxycinamate and octyl p-methoxycinamate; salycilic acid derivatives, for example, octyl salycilate and phenyl salycilate; urocanic acid and derivatives thereof; 4-tert-butyl-4'-methoxydibenzoylmethane, 2-(hydroxy-5'-methylphenyl)benzotriazole and methyl anthranilate.

The above-mentioned extinguishing agents includes glycyrretinic acid and derivative thereof, glycylrrhetinic acid and derivatives thereof, allantoin, hydrocortisone acetate and azulene.

The above-mentioned sequestrants include ethylenediamine tetraacetate, and sodium salt thereof, phosphoric acid, citric acid, ascorbic acid, succinic acid, gluconic acid sodium polyphosphate and sodium metaphospahte.

The above-mentioned lower alcohols include ethyl alcohol, propyl alcohol, ethyleneglycol, and diethyleneglycol.

The above-mentioned saccharides include glucose, lactose, white sugar, starch, carboxymethyl starch, and cyclodextrin.

The above-mentioned amino acid compounds include aspartic acid and salts thereof, alanine, arginine, lisin lysine and salts thereof, glycine, cystine, threonine, serine and methionine.

The above-mentioned organic amine compounds include monoethanolamine, diethanolamine, triethanolamine, diisopropanolamine and triethylamine.

The above-mentioned synthetic resin emulsions includes emulsions of polyacrylic acid ester copolymers and polyvinyl acetate.

The above-mentioned pH adjusters include citric acid, hydrochloric acid, sulfuric acid, phosphoric acid, sodium hydroxide and ammonia.

The above-mentioned skin nutritive agents include vitamins A, B1, B2, B6 and E and derivatives thereof, pantothenic acid and derivatives thereof and biotin.

The above-mentioned antioxidants include vitamin E, dibutylhydroxytolunene, butylhydroxy anisole, and gallic acid esters.

The above-mentioned antioxidant assistants include ascorbic acid, phytic acid, cephalin and aleic acid.

The substances mixed with the refined product of the surface active compounds of the present invention are not limited to the above-mentioned substances.

In the preparation of the cosmetic or detergent from the refined product of the present invention, the refined product is mixed with desired additional component by a conventional procedure.

EXAMPLE

The present invention will be further illustrated by the following examples which are not intended to limit the scope of the present invention in any way.

Production Example 1

Preparation of lauric acid monoisopropanolamide Using, as a Starting Material, a fatty acid ester Methyl laurate in an amount of 214 g was mixed with 76 g of isopropanolamine and 1 g of sodium methoxide, and the resultant reaction system was heat-stirred under a pressure of 2.7 kPa at a temperature of 90° C. for 6 hours while the resultant by-product consisting of methyl alcohol was distilled away under reduced pressure from the reaction system, to prepare 258 g of lauric acid isopropanolamide.

Production Example 2

Preparation of lauric acid monoisopropanolamide by Using, as a Starting Material, a fatty acid Lauric acid in an amount of 200 g was mixed with 76 g of isopropanol, and the resultant reaction system was heat-stirred under a pressure of 0.3 to 33.3 kPa at a temperature of 150° C. for 5 hours while the resultant by-product consisting of water was distilled away under reduced pressure from the reaction system, to prepare 258 g of lauric acid isopropanolamide.

Production Example 3

Preparation of 2-undecyl-4-methyl-2-oxazoline

The lauric acid monoisopropanolamide produced in Production Example 1 and in an amount of 258 g was heat-stirred under a reduced pressure of 26.7 kPa at a temperature of 190° C. for 4 hours, and then pressure of the reaction system is further reduced and the reaction system was subjected to a distillation under the further reduced pressure of 0.5 kPa at a temperature of 157 to 158° C. As a distilled fraction, 2-undecyl-4-methyl-2-oxazoline was collected with a yield of 97 g.

<Identification>

It was confirmed that the resultant oxazoline compound is 2-undecyl-4-methyl-2-oxazoline by the $^1$H-NMR spectroscopy and the infrared absorption spectroscopy.

The $^1$H-NMR spectrum measurement was carried out by using NMR spectrometer (model: AC250P, made by BRUKER), and the infrared absorption spectrum measurement was carried out by using FT-IR Spectrometer (model: PARAGON 1000, made by PERKIN ELMER).

In the measured $^1$H-NMR spectra, (CDCl$_3$, 250 MH$_z$) absorptions were found at the following bonds:

δ=0.85 to 0.90 (t, 3H, C$\underline{H}_3$CH$_2$), 1.17 to 1.20 (d, 3H, OCH(C$\underline{H}_3$)), 1.25 to 1.33 (m, 16H, CH$_3$(C$\underline{H}_2$)$_8$), 1.38 to 1.64 (m, 2H, CH$_3$(CH$_2$)$_8$C$\underline{H}_2$), 2.21 to 2.30 (m, 2H, CH$_3$(CH$_2$)$_9$C$\underline{H}_2$), 3.32 to 3.95 (m, 2H, NC$\underline{H}_2$CH), 4.58 to 4.72 (m, 1H, OC$\underline{H}$(CH$_3$))

In the measured infrared absorption spectra (liquid film method), the following characteristic absorptions were found at the following bands:

2850 to 2930 cm$^{-1}$ (νV—H), 1650 to 1670 cm$^{-1}$ (νC=N), 1170 to 1230 cm$^{-1}$ (νC—O),

Example 1

Preparation of a Refined Product of polyoxvpropylene (1.5) lauric acid isopropanolamide The lauric acid monoisopropanolamide produced in Production Example 1 and in an amount of 258 g was mixed with 87 g of propylene oxide, and the resultant mixture was placed in an autoclave, and heat-stirred at 120° C. for 3 hours, to prepare a reaction mixture containing polyoxypropylene. (1.5) lauric acid isoporopanolamide in a yield of 345 g.

A sample of the resultant reaction mixture was subjected to a quantitative analysis to determine the content of oxazoline compound.

Further, the reaction mixture containing polyoxypropylene (1.5) lauric acid isopropanolamide in an amount of 100 g was mixed with 10 g of a 5% aqueous sodium hydroxide solution, and the mixture was heated at 80° C. for one hour while stirring the. mixture. Then, this reaction mixture was distilled under 2.7 kPa at 80° C. for one hour, to such an extent that the content of water in the reaction mixture decreased to 0.1% by mass or less to prepare a refined product of polyoxypropylene (1.5) lauric acid isopropanolamide having a decreased content of the oxazoline compound.

Example 2

Preparation of a Refined Product of polyoxypropylene (3) lauric acid isopropanolamide The lauric acid monoisopropanolamide produced in Production Example 2 and in an amount of 258 g was mixed with 174 of propylene oxide., and the resultant mixture was placed in an autoclave, and heated at 120° C. for 3 hours while stirring the mixture, to prepare a reaction mixture containing polyoxypropylene (3) lauric acid isopropanolamide in a yield of 432 g.

Further, the reaction mixture containing polyoxypropylene (3) lauric acid isopropanolamide in an amount of 100 g was mixed with 10 g of a 5% aqueous sodium hydroxide solution, and the mixture was heated at 80° C. for one hour while stirring the mixture. Then, this reaction mixture was distilled under 2.7 kPa at 80° C. for one hour, to such an extent that the content of water in the reaction mixture decreased to 0.1% by mass or less to prepare a refined product of polyoxypropylnene (3) lauric acid isopropanolamide having a decreased content of the oxazoline compound.

Comparative Example 1

Preparation of Non-refined polyoxvpropylene (2) lauric acid monoisopropanolamide The lauric acid isopropanolamide produced in Production Example 1 and in an amount of 258 g was mixed with 116 g of propylene oxide, and the resultant mixture was placed in an autoclave, and heated at 150° C. for 3 hours while stirring the mixture, to prepare a reaction mixture containing polyoxypropylene (2) lauric acid isporopanolamide in a yield of 374 g.

Comparative Example 2

Preparation of Non-refined polyoxypropylene (1.5) lauric acid isopropanolamide The lauric acid monoisopropanolamide produced in Production Example 1 and in an amount of 258 g was mixed with 87 g of propylene oxide, and the resultant mixture was placed in an autoclave, and heat-stirred at 180° C. for 3 hours, to prepare a reaction mixture containing polyoxypropylene (1.5) lauric acid isopropanolamide in a yield of 345 g.

Example 3

Preparation of a Refined Product of polyoxypropylene (2) lauric acid isopropanolamide, having a Decreased Content of oxazoline Compound The non-refined polyoxypolypropylene (2) lauric acid isopropanolamide prepared in Comparative Example 1 and in an amount of 100 g was mixed with 10 g of a 5% aqueous sodium hydroxide solution, and the mixture was heated at 80° C. for one hour while stirring the mixture. Then, this reaction mixture was distilled under 2.7 kPa at 80° C. for one hour, to such an extent that the content of water in the reaction mixture decreased to 0.1% by mass or less, to prepare a refined product of polyoxypropylnene (2) lauric acid isopropanolamide having a decreased content of the oxazoline compound.

Example 4

Preparation of a Refined Product of polyoxyypropylene (1.5) lauric acid isopropanolamide, Having a Decreased Content of oxazoline Compound The non-refined polyoxypolypropylene (1.3) lauric acid isopropanolamide prepared in Comparative Example 2 and in an amount of 100 g was mixed with 10 g of a 5% aqueous-sodium-hydroxide-solution, and the mixture was heated at 80° C. for one hour while stirring the mixture. Then, this reaction mixture was distilled under 2.7 kPa at 80° C. for one hour, to such an extent that the content of water in the reaction mixture decreased to 0.1% by mass or less to prepare a refined product of polyoxypropylnene (1.5) lauric acid isopropanolamide having a decreased content of the oxazoline compound.

Example 5

Preparation of polyoxvpropylene (1.5) lauric acid isopropanolamide by a Low Temperature Reaction The lauric acid monoisopropanolamide produced in Production Example 1 and in an amount of 258 g was mixed with 87 g of propylene oxide, and the resultant mixture was placed in an autoclave, and heated at 100° C. for 6 hours while stirring the mixture, to prepare a reaction mixture containing polyoxypropylnene (1.5) lauric acid isopropanolamide in a yield of 345 g.

Comparative Example 3

Preparation of Non-refined polyoxvpropylene (1) lauric acid isopropanolamide The lauric acid isopropanolamide prepared in Production Example 1 and in an amount of 58 g was placed together with 58 g of propylene oxide in an autoclave, and the resultant reaction mixture was stirred at a temperature of 180° C. for 3 hours, to prepare a reaction mixture containing polyoxypropylnene (1) lauric acid isopropanolamide in an yield of 316 g.

Tests (1) Analysis

The products of Production Examples 1 and 2, Examples 1 to 5 and Comparative Examples 1 to 3 were subjected to a gas chromatographic analysis using a gas chromatographic analyses mark by HEWLETT-PACKARD CO., under the conditions shown below, to determine the contents of the oxazoline compound.

(GLC Conditions)

Carrier gas: helium

Column: Capillary column ULTRA 1 made by HEWLETT-PACKARD CO. 50 m×0.2 mm×0.33 μ.

Inlet temperature: 280° C.

Initial temperature: 100° C.

Temperature increase rate: 10° C./min.

Final temperature: 300° C.

The analysis results are shown in Table 1.

(2) Test of Stability in Storage

The stability in storage of each of the surfactants of Examples 1 to 5 and Comparative Examples 1 to 3 was evaluated by the following method.

(Evaluation Method)

A sample was placed in a 100 ml glass bottle and sealed with a cap and then stored in a constant temperature vessel at a temperature of 50° C. for one month. Then, the colors (APHA) of the sample at 50° C. before and after storage were measured. The change in color of the sample was evaluated as follows.

| Class | Color change |
|---|---|
| 3 | Change in color (APHA) is 100 or less. |
| 2 | Change in color (APHA) is more than 100 and not more than 200. |
| 1 | Change in color (APHA) is more than 200. |

The evaluation results are shown in Table 1.

(3) Sensory Test

The sensory properties of each of the surfactants of Examples 1 to 5 and Comparative Examples 1 to 3 were evaluated by the following test.

(Evaluation Method)

The organoleptic properties of each sample of the surfactants were evaluated by 10 testers including 5 men and 5 women, 20 to 40 years old, by the following method.

Each sample was stored in a constant temperature vessel at a temperature 25° C. or 50° C. for one day, and then the smell of the stored sample was evaluated with the following marks.

| Merit marks | Smell |
|---|---|
| 5 | No smell is generated after 25° C. and 50° C. storages, respectively. |
| 4 | No smell is generated after 25° C. storage and slight smell is generated after 50° C. storage. |
| 3 | Slight smell is generated after 25° C. and 50° C. storages, respectively. |
| 2 | Slight smell is generated after 25° C. storage and apparent smell is generated after 50° C. storage. |
| 1 | Apparent smell is generated after 25° C. and 50° C. storages, respectively. |

With respect to each sample, an average of the numbers of the merit marks given by the 10 evaluation members was calculated.

The evaluation results are indicated by the following classes.

| Class | Average number of meric marks |
|---|---|
| 4 | 4.0 or more |
| 3 | 3.0 or more and not more than 4.0 |
| 2 | 2.0 or more and not more than 3.0 |
| 1 | Less than 2.0 |

The results are shown in Table 1.

TABLE 1

| | | Content of oxazoline compound (% by mass) | Storage stability | Organoleptic test (Smell generation) |
|---|---|---|---|---|
| Production Example | 1 | Not detected | — | — |
| | 2 | Not detected | — | — |
| Example | 1 | Not detected | 3 | 3 |
| | 2 | Not detected | 3 | 3 |
| | 3 | 0.03% | 3 | 3 |
| | 4 | 0.06% | 3 | 2 |
| | 5 | 0.05% | 3 | 3 |
| Comparative Example | 1 | 0.16% | 2 | 2 |
| | 2 | 2.5% | 1 | 1 |
| | 3 | 4.7% | 1 | 1 |

Examples 6 to 8 and Comparative Examples 4 to 7

In each of Examples 6 to 8 and Comparative Examples 4 to 7, the polyoxypropylene (1.5) lauric acid isopropanolamide produced in Example 1 and the oxazoline compound produced in Production Example 3 were mixed with each other in the mixing ratio shown in Table 2, and a sample of the resultant mixture was subjected to tests for color change and stability in storage by the above-mentioned test methods.

Also, each sample was subjected to a determination of the content of the oxazoline compound in the mixture by a high performance liquid chromatography under the following measurement condition.

(Experimental Conditions)
Pump: Model: PU-980, made by NIHON BUNKO K.K.
UV detector: Model: UV-970
Degasser: Model: DG-980-50
Column: Model: Inertsil ODS-2 4.6 mm×250 mm made by GL SCIENCE K.K.
Mobile phase: Acetonitrile-0.03M aqueous hydrogen sodium phosphate solution (pH=2.1), (50:50)
Flow rate: 1 ml/min.
Amount of Sample: 20 µ liter
Column temperature: 40° C., constant
Detector (Detecting wavelength): UV detector (210 nm)
The test results are shown in Table 2.

TABLE 2

| | | Mixed components (mass %) | | Amount of detected oxazoline compound (%) | test result | |
|---|---|---|---|---|---|---|
| | | Product of Example 1 | Product of Production Example 3 | | Color | Smell |
| Example | 6 | 100 | 0 | Not detected | 3 | 3 |
| | 7 | 99.95 | 0.05 | 0.05 | 3 | 3 |
| | 8 | 99.9 | 0.1 | 0.1 | 3 | 3 |
| Comparative Example | 4 | 99.8 | 0.2 | 0.2 | 2 | 3 |
| | 5 | 99.5 | 0.5 | 0.5 | 2 | 2 |
| | 6 | 99.0 | 1.0 | 1.0 | 2 | 1 |
| | 7 | 95.0 | 5.0 | 5.0 | 1 | 1 |

From Table 2, it was confirmed that the determination method of the content of the oxazoline compound has a high reliability.

Conventional polyoxypropylene fatty acid isopropanol amide nonionic surfactants exhibit on rare occasions a weak sensitization on skin. However, the polyoxypropylene fatty acid isopropanolamide produced in each of Examples 1 to 5 and having a very low content of the oxazoline compound exhibited completely no skin sensitization. In comparison with this, the non-refined product of Comparative Example 2, which should be compared with Example 4, exhibited a weak skin sensitization. From this fact, it was confirmed that a product having a high safety can be obtained by decrease the content of the oxazoline compound in accordance with the present invention.

Example 9 and Comparative Example 8

In each of Example 9 and Comparative Example 8, a liquid detergent was prepared in accordance with the composition shown in Table 3.

The stability of color in storage and the prevention of smell generation of the liquid detergent were tested. The test results are shown in Table 3.

TABLE 3

| Composition | Example 9 (Part by mass) | Comparative Example 8 (Part by mass) |
|---|---|---|
| Polyoxyethylene (2) laurylether sulfate Na salt (25% aqueous solution) | 60.0 | 60.0 |
| N-lauroyl sarcosine sodium (30% aqueous solution) | 16.6 | 16.6 |
| Product of Example 1 | 4.0 | — |
| Product of Comparative Example 2 | — | 4.0 |
| Citric acid | Amount necessary to adjust pH to 6.5 | Amount necessary to adjust pH to 6.5 |

TABLE 3-continued

| Composition | Example 9 (Part by mass) | Comparative Example 8 (Part by mass) |
| --- | --- | --- |
| EDTA·2Na | 0.1 | 0.1 |
| Purified water | Amount necessary to make total to 100 parts | Amount necessary to make total to 100 parts |
| Stability of color | 3 | 2 |
| Prevention of smell generation | 4 | 2 |

The liquid detergent of Example 9 had an excellent stability of color during storage and a highly preventive to smell generation.

Example 10

A conditioning shampoo was prepared in the following composition.

| | |
| --- | --- |
| 30% solution of lauric acid amide propylamineoxide | 16.60% |
| 30% solution of N-lauroyl-N-methyl-β-alanine sodium | 23.30% |
| 30% solution of N-lauroyl-β-alanine sodium | 16.60% |
| Product of Example 1 | 3.00% |
| Cation-modified cellulose | 0.20% |
| Allantoin | 0.80% |
| Methylparaben | 0.20% |
| Propylparaben | 0.10% |
| Citric acid | Amount necessary to adjust pH to 6.2 |
| Purified water | Balance |

All of the components are placed in a reactor and heated to 80° C. while stirring the resultant mixture, and after it was confirmed that the mixture was completely dissolved, the mixture was cooled to 40° C. while stirring the mixture. A target shampoo composition was obtained. It was confirmed that as a result of an accelerated storage test at 40° C. for 3 months, no change in color and smell was found.

Example 11

A pearly shampoo was prepared in the following composition.

| | |
| --- | --- |
| 30% solution of lauric acid amide propylacetic acid betaine | 26.60% |
| 30% solution of N-coconut oil fatty acid gluramic acid TEA salt | 10.00% |
| 30% solution of N-lauroylsacrosine sodium | 20.00% |
| Product of Example 2 | 5.00% |
| Glycerol | 1.50% |
| — | 0.80% |
| Ethyleneglycol distearate | 1.50% |
| Methylparaben | 0.20% |
| Propylparaben | 0.1% |
| Citric acid | Amount necessary to adjust pH to 7.0 |
| Purified water | Balance |

All of the components are placed in a reactor and heated to 80° C. while stirring the resultant mixture, and after it was confirmed that the mixture was completely dissolved, the mixture was cooled to 40° C. while stirring the mixture. A target shampoo composition was obtained. It was confirmed that the shampoo composition exhibited a light yellow color and a pearl-like gloss, and thus the polyoxypropylene fatty acid isopropanolamide is a surfactant which can impart a pearl-like gloss to the shampoo composition.

Example 12

A transparent shampoo was prepared in the following composition.

| | |
| --- | --- |
| 30% solution of coconut oil fatty acid acylmethyltaurine sodium salt | 12.5% |
| 30% solution of lauric acid amide propylacetic acid betaine | 12.5% |
| 25% solution of POE(2) laurylether sulfate Na salt | 30.0% |
| Product of Example 2 | 6.0% |
| Dipotassium salt of glycyrrhizinic acid | 0.1% |
| Citric acid | Amount necessary to adjust pH to 6.5 |
| Methylparaben | 0.1% |
| Purified water | Balance |

All of the components are placed in a reactor and heated to 80° C. while stirring the resultant mixture, and after it was confirmed that the mixture was completely dissolved, the mixture was cooled to 40° C. while stirring the mixture. A target shampoo composition was obtained. It was confirmed that as a result of an accelerated storage test at 40° C. for 3 months, no change in color and smell was found.

Example 13

A body shampoo was prepared in the following composition.

| | |
| --- | --- |
| 25% solution of POE(2) laurylether sulfate Na salt | 28% |
| 85% solution of monolauryl phosphate ester Na salt | 5.9% |
| Coconut oil fatty acid | 2.5% |
| Product of Example 2 | 6.0% |
| Triethanolamine | Amount necessary to adjust pH to 8.7 |
| Ethyleneglycol distearate | 0.5% |
| Methylparaben | 0.1% |
| Purified water | Balance |

All of the components are placed in a reactor and heated to 80° C. while stirring the resultant mixture, and after it was confirmed that the mixture was completely dissolved, the mixture was cooled to 40° C. while stirring the mixture. A target shampoo composition was obtained. It was confirmed that as a result of an accelerated storage test at 40° C. for 3 months, no change in color and smell was found.

Example 14

A transparent gel state detergent composition was prepared in the following composition.

| | |
|---|---|
| Lauric acid | 7.4% |
| Myristic acid | 8.5% |
| L-arginine | 14.1% |
| Product of Example 1 | 5.00% |
| Dipotassium salt of glycyrrhizinic acid | 0.10% |
| Purified water | Balance |

All of the components are placed in a reactor and heated to 80° C. while stirring the resultant mixture, and after it was confirmed that the mixture was completely dissolved, the mixture was cooled to 60° C. while stirring the mixture, and then transferred to a container and further cooled to 30° C. by leaving the container to stand. A target shampoo composition was obtained. It was confirmed that after storing the composition at 40° C. for 3 months, the liquid state was stably kept and no coloration was found.

Example 15

A soap composition was prepared in the following composition.

| | |
|---|---|
| Soap chips (water content - 13%) | 96.9% |
| Product of Example 1 | 3.00% |
| Titanium dioxide | 0.10% |

All of the components are placed in a mixer, and kneaded, and then passed through a three roller machine three times to make uniform the quality of the mixture. The mixture was supplied to an extruder to provide a soap bar. The soap bar was shaped into a desired foam. It was confirmed that after storage at 50° C. for 3 months, the color of the soap was the same as a comparative soap prepared from only the same soap chips as mentioned above.

Example 16

A transparent soap composition was prepared in the following composition.

| | |
|---|---|
| Tallow fatty acid sodium salt | 32.0% |
| Coconut oil fatty acid sodium salt | 8.0% |
| N-cocoyl-glutamic acid sodium salt | 2.0% |
| Concentrated glycerol | 6.0% |
| White sugar | 10.0% |
| Ethyl alcohol | 20.0% |
| Product of Example 1 | 1.0% |
| Dipotassium salt of glycyrrhizinic acid | 0.1% |
| Coloring matter | Small amount |
| Water | 20.9% |

All of the components are placed in a reactor and heated to 80° C. while stirring the resultant mixture, and after it was confirmed that the mixture was completely dissolved, the mixture was cooled and solidified. The solid soap composition was cut into pieces having desired shape and dimensions. The soap pieces were dried at room temperature for about 40 days by gradually evaporating away water and ethyl alcohol from the pieces. A target transparent soap composition was obtained. It was confirmed that the inclusion of the product of Example 2 in the soap composition enables the foam particle size to be decreased and the feeling in washing with the soap composition to be improved.

Where the product of Example 1 was replaced by the product of Comparative Example 2, the resultant comparative soap composition wad identical in foaming property and hand feeling to this example. However, after a sample of the comparative soap composition was subjected to an accelerated test at 40° C. for 3 months, the tested sample was colored yellow, whereas no change in color of the transparent soap of Example 16 occurred.

INDUSTRIAL APPLICABILITY

The refined product of polyoxypropylene fatty acid isopropanolamide surfactant of the present invention exhibits a high stability in storage and a small change in smell and thus is useful for practice. The refined product can be produced with a high efficiency in accordance with the process of the present invention. Also, the detergent composition containing the refined product of the present invention is very stable in color and smell and exhibit excellent storage stability, thickening property, foaming property foam stability, emulsifying property, dispersing property and dissolving property.

The invention claimed is:

1. A process for producing a refined product of a polyoxypropylene fatty acid isopropanolamide surfactant comprising addition reacting a fatty acid monoisopropanolamide represented by the general formula (III):

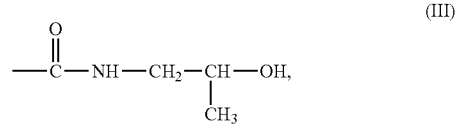

(III)

in which formula (III), $R^1$ represents an alkyl or alkenyl group having 5 to 19 carbon atoms, with propylene oxide in a molar amount of 0.5 to 10 times that of the compound of the formula (III), to product a reaction mixture of a surface active polyoxylproplyene fatty acid isopropanolamide compound of the general formula (I) with, as a side reaction product, an oxazoline compound of the formula (II):

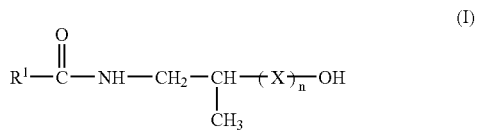

(I)

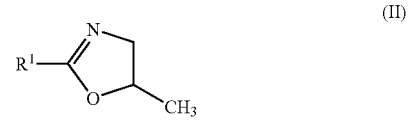

(II)

in which formulae (I) and (II), $R^1$ is as defined above, X represents an oxypropylene group and n represents an average number of moles of the addition-reacted X group of 0.5 to 10;

mixing water or an aqueous alkaline solution into the reaction mixture, to prepare a refining reaction system;

heating the refining reaction system to a temperature of 50 to 100° C. to hydrolyze the oxazoline compound of the general formula (II) and to thereby reduce the content of the oxazoline compound of the general formula (II) in the reaction mixture of 0.1% by mass or less based on the mass of the compound of the formula (I); and collecting the refined product of polyoxypropylene fatty acid isopropanolamide surfactant comprising the compound of the formula (I) from the reaction system.

2. The process for producing a refined product of a polyoxypropylene fatty acid isopropanolamide surfactant as claimed in claim 1, wherein the pH value of the refining reaction system is adjusted to 7.5 to 12.0.

3. The process for producing a refined product of a polyoxypropylene fatty acid isopropanolamide surfactant as claimed in claim 1 or 2, wherein the aqueous alkaline solution to be contained in the refining reaction system is selected from aqueous solutions of at least one member selected from sodium hydroxide, potassium hydroxide and lithium hydroxide.

* * * * *